United States Patent
Kohr et al.

(10) Patent No.: US 9,789,112 B2
(45) Date of Patent: Oct. 17, 2017

(54) ORAL PHARMACEUTICAL FILM FORMULATION FOR BITTER TASTING DRUGS

(71) Applicant: HEXAL AG, Holzkirchen (DE)

(72) Inventors: Thomas Kohr, Holzkirchen (DE); Petra Obermeier, Holzkirchen (DE)

(73) Assignee: HEXAL AG, Holzkirchen (DE)

( * ) Notice: Subject to any disclaimer, the term of this patent is extended or adjusted under 35 U.S.C. 154(b) by 0 days.

(21) Appl. No.: 15/179,213

(22) Filed: Jun. 10, 2016

(65) Prior Publication Data

US 2016/0279134 A1 Sep. 29, 2016

Related U.S. Application Data

(62) Division of application No. 13/881,613, filed as application No. PCT/EP2011/068813 on Oct. 27, 2011, now abandoned.

(30) Foreign Application Priority Data

Oct. 28, 2010 (DE) .................. 10 2010 049 708

(51) Int. Cl.

| | |
|---|---|
| *A61K 31/519* | (2006.01) |
| *A61K 47/38* | (2006.01) |
| *A61K 47/18* | (2017.01) |
| *A61K 47/26* | (2006.01) |
| *A61K 47/08* | (2006.01) |
| *A61K 47/14* | (2017.01) |
| *A61K 47/06* | (2006.01) |
| *A61K 31/495* | (2006.01) |
| *A61K 31/4045* | (2006.01) |
| *A61K 9/70* | (2006.01) |
| *A61K 9/00* | (2006.01) |
| *A61K 47/02* | (2006.01) |
| *A61K 47/10* | (2017.01) |

(52) U.S. Cl.
CPC .......... *A61K 31/519* (2013.01); *A61K 9/0056* (2013.01); *A61K 9/7007* (2013.01); *A61K 31/4045* (2013.01); *A61K 31/495* (2013.01); *A61K 47/02* (2013.01); *A61K 47/06* (2013.01); *A61K 47/08* (2013.01); *A61K 47/10* (2013.01); *A61K 47/14* (2013.01); *A61K 47/18* (2013.01); *A61K 47/26* (2013.01); *A61K 47/38* (2013.01)

(58) Field of Classification Search
None
See application file for complete search history.

(56) References Cited

U.S. PATENT DOCUMENTS

| | | | |
|---|---|---|---|
| 5,846,557 A | 12/1998 | Eisenstadt et al. | |
| 2003/0211136 A1 | 11/2003 | Kulkarni et al. | |
| 2006/0024335 A1 | 2/2006 | Roger | |
| 2007/0178123 A1 | 8/2007 | Levenson et al. | |
| 2009/0047330 A1 | 2/2009 | Bangalore | |
| 2010/0240724 A1 | 9/2010 | Chang et al. | |

FOREIGN PATENT DOCUMENTS

| | | |
|---|---|---|
| CN | 101574330 A | 11/2009 |
| DE | 10207394 A1 | 9/2003 |
| EP | 1621080 A1 | 2/2006 |
| EP | 2008530 A1 | 12/2008 |
| WO | 8501656 A1 | 4/1985 |
| WO | 2004019885 A2 | 3/2004 |
| WO | 2004043165 A1 | 5/2004 |
| WO | 2006013416 A1 | 2/2006 |
| WO | 2006072921 A2 | 7/2006 |
| WO | 2007009800 A2 | 1/2007 |
| WO | 2007009801 A2 | 1/2007 |
| WO | 2007089652 A2 | 8/2007 |
| WO | 2008040534 A2 | 4/2008 |
| WO | 2009052421 A1 | 4/2009 |
| WO | 2012055944 A1 | 5/2012 |

OTHER PUBLICATIONS

Japanese Office Action for the Corresponding Japanese Patent Application No. 2013-535427, dated May 10, 2016 (7 Pages).
Leffingwell, "Cooling Ingredients and Their Mechanism of Action", Handbook of Cosmetic Science and Technology, 3rd ed., 2009, pp. 661-675.
German Office Action dated Apr. 20, 2015 issued in German Patent Application No. 102010049708.8.
Sharma et al., "Taste Masking Technologies: A Review", International Journal of Pharmacy and Pharmaceutical Sciences, 2010, vol. 2, Issue 2, pp. 1-8.
Ley, "Masking Bitter Taste by Molecurels", Chem. Percept., 2008, vol. 1, DOI: 10.1007/s12078-008-9008-2, pp. 58-77.
International Search Report for International Application No. PCT/EP2011/068813, (dated Feb. 14, 2012).
Japanese Office Action dated Jul. 7, 2015 issued in Japanese Patent Application No. 2013-535427.

*Primary Examiner* — Ernst V Arnold
*Assistant Examiner* — Kyung Sook Chang
(74) *Attorney, Agent, or Firm* — Lucas & Mercanti, LLP

(57) ABSTRACT

The invention relates to a pharmaceutical film formulation comprising one or more bitter-tasting drug(s) or pharmaceutically acceptable salts thereof, one or more film formers, a bitterness masker containing one or more inorganic and/or organic salt(s) and at least two monocyclic monoterpenes, and one or more sweetening agents.

22 Claims, No Drawings

ORAL PHARMACEUTICAL FILM FORMULATION FOR BITTER TASTING DRUGS

CROSS-REFERENCE TO RELATED APPLICATIONS

This application is a Division of U.S. application Ser. No. 13/881,613, filed Apr. 25, 2013, which is a 371 of PCT International Application No. PCT/EP2011/068813, filed Oct. 27, 2011, which claims the benefit of German Application No. 102010049708.8, filed Oct. 28, 2010, the contents of each of which are incorporated herein by reference.

FIELD OF THE INVENTION

The present invention relates to a pharmaceutical formulation that is based on a non-muco-adhesive, oral, rapidly disintegrating, preferably single-layer film, and contains one or more bitter tasting drugs or pharmaceutically acceptable salts thereof, together with appropriate excipients to mask the taste.

BACKGROUND OF THE INVENTION

The peroral administration of drugs still represents the most commonly used method of administration. For patient compliance with peroral administration human gustatory and olfactory sense is of great importance.

Traditional dosage forms such as tablets or capsules, which are to a great extent used as carriers for the oral delivery of drugs, usually are indeed tasteless, however require in common usage, that the patient keeps at hand a fluid, with which he can take this dosage form. Because of discomfort in swallowing especially in elder patients and children, this form of intake is often problematic. Moreover, a discrete intake is hardly possible. This sometimes leads to poor compliance and can thus jeopardize the success of therapy.

Even in groups of patients with mental diseases, in which the monitoring of the actual intake of their medication is essential, the administration of conventional dosage forms such as tablets or capsules is not unproblematic. Because of their delayed resolution they can be easily removed from the mouth, without being noticed by the supervising medical personnel.

To overcome the problems described, pharmaceutical dosage forms, such as granules or oral films have been developed, which can be taken without liquid supply and which disintegrate rapidly in the oral cavity. Oral films are characterized for example by the fact that they have a low layer thickness and a large surface area, and remain stuck to oral mucosa and disintegrate very quickly in the oral cavity. They can be taken always and everywhere discretely according to the patient's needs, without the need of additional, simultaneous intake of fluid.

Oral films and methods of preparation thereof are described, for example in WO2007/009800 and WO2007/009801.

A particular problem with the administration of bitter tasting drugs in the form of an orally dispersible film poses their release in the oral cavity or on the tongue of the patient. Because of the bitter taste of the respective drugs, taking such formulations is often perceived as very unpleasant, leading to an impairment of compliance. The masking of the bitter taste of the drugs used, i. e. the flavor optimization of oral films is therefore of great importance in the development of this dosage form.

Method for taste masking in pharmaceutical preparations generally include for example the use of coatings, the production of granules, the use of sweeteners, the microencapsulation, the use of taste suppressive and taste enhancer, the preparation of solid dispersions, the use of ion exchange resins, the use of viscosity-increasing substances, the complex formation, the use of pH modifying agents, and the use of adsorbents (see for example Ayenew, Z. et al., Trends in Pharmaceutical Taste Masking Technologies: A Patent Review, Recent Patents on Drug Delivery and Formulation 2009, 3, 26-39).

Non-mucoadhesive, orally disintegrating films as pharmaceutical dosage forms are described in WO 2008/040534. The drugs released therefrom are however not absorbed via the oral mucosa. The objective in the for development of these films was instead the provision of a generic dosage form, the pharmacokinetic properties of which are similar to those of orally administered dosage forms, after the administration of which there is an absorption of the released drugs in the gastrointestinal tract, such as tablets, capsules, liquid suspensions or orally disintegrating tablets. Beside a film former the films disclosed in WO 2008/040534 may also contain flavorings, sweeteners and taste-masking agents. As taste-masking agents amino alkyl methacrylate copolymers such as Eudragit E PO and cyclodextrin are described. The list of drugs that is described in WO 2008/040534 for administration with the film formulation disclosed therein contains i. a. the following bitter tasting drugs: risperidone, sildenafil, vardenafil, sumatriptan, zolmitriptan, naratriptan, cetirizine and dextromethorphan.

In US 2003/0211136 rapidly disintegrating films for oral administration are disclosed, which are in particular characterized by the presence of a sweetener for taste masking. As suitable sweeteners, natural and artificial sweeteners are described, such as monosaccharides, disaccharides and polysaccharides, saccharin salts, sweeteners based on dipeptide, such as sweeteners derived from L-aspartic acid, and protein based sweeteners. Further suitable sweeteners are sucralose, aspartame, acesulfame potassium, neotame, saccharin, xylitol, and mixtures thereof. Bitter tasting drugs, which are mentioned in US 2003/0211136, are i. a. dextromethorphan, diphenhydramine, cetirizine and nicotine.

Another film formulation for oral administration of a bitter tasting drug is described in WO 2006/013416. Therein a complex is used for taste masking, which consists of a taste receptor blocker, a taste receptor competitor and a sweetener as well as optionally of a flavoring agent. Hydrogenated ethoxylated glycerol esters are described as suitable taste receptor blockers. The taste receptor competitor generally include substances that give a salty or a sour taste, such as citric acid and phosphoric acid or their sodium and potassium salts as well as sodium chloride and hydroxy acids, such as glycolic acid, lactic acid and tartaric acid, etc., and their salts. As sweeteners both substances are suitable whose sweetness effect occurs immediately, as well as substances whose sweetness effect occurs only delayed. Examples are saccharin, sucralose, neotame, alitame, aspartame and cyclamate, etc. for sweeteners with immediate effect as well as monoammonium glycyrrhizinate for sweeteners with delayed sweetness effect. As bitter tasting drugs dextromethorphan, chlorhexidine, guaifenesin, pseudoephedrine, caffeine, peroxides, atorvastatin, aspirin, paracetamol, diphenhydramine, doxylamine, sildenafil citrate and loperamide are disclosed in WO 2006/013416.

A polymer-based edible film formulation with sildenafil citrate, tadalafil, or vardenafil as drug contained therein is disclosed in US 2009/0047330. For taste masking the use of cyclodextrins or the encapsulation of the drugs is proposed. Besides the film formulation may also contain flavoring agents, such as menthol and the like, as well as sweeteners, such as acesulfame potassium, sucralose, aspartame and glyrrhizin.

A fundamental problem of these formulations is that the effective covering of taste of extremely bitter tasting drugs such as sildenafil, is difficult to achieve—if at all—by conventional methods, i.e. solely by the addition of sweeteners, flavoring agents, etc. This applies in particular, if drug concentrations of more than 50 or 60% by weight related to the total weight of the formulation are used. In such cases it is usually necessary to coat the particular drug in a complex method (see Section 4. Factors affecting selection of taste masking technology: A. Extend of bitter taste in Ayenew, Z. et al., Trends in Pharmaceutical Taste Masking Technologies: A Patent Review, Recent Patents on Drug Delivery and Formulation 2009, 3, 26-39).

The object of the present invention is accordingly, to provide a film formulation for oral administration that after taking in the oral cavity disintegrates quickly and which enables effective taste masking of high concentrations of extremely bitter tasting drugs contained therein and which can at the same time be produce both simply and inexpensively.

Surprisingly it has now been found that the specific combination of one bitterness masker containing one or more inorganic and/or organic salt(s) and a plurality of monocyclic monoterpenes, and one or more sweetener(s) and optionally one or more flavoring agent(s) is suitable for effective taste masking even of extremely bitter tasting drugs in films suitable for oral administration.

Likewise, it was surprisingly found that based on this combination, an acceptably tasting single-layer film or a single-layer preparation, respectively, comprising one or more film formers and one or more extremely bitter tasting drug(s) can be formed.

It was found that the bitter taste sensation induced by the one or more drug(s) formulated in a film is more intense and unpleasant, the longer the film remains in the oral cavity, i. e. the greater the retention time of the drug or the drugs is in the oral cavity. In order to minimize the intensity of the bitter taste, it is thus desirable to reduce the time period between the taking of the oral film and its complete disintegration in the oral cavity. This criterion can in general be met in that the oral film is kept very thin, i.e. has a large surface to volume ratio.

Especially very thin film formulations, however have the disadvantage that they dry out very quickly, sometimes even during film synthesis, and then lose their flexibility and become brittle. This negatively affects the manufacturing process and is also very undesirable in application. In order to ensure the flexibility necessary for manufacture and for handling by the patient, in particular of very thin film formulations, permanent moisture content in the film is thus necessary. It appeared that a water content of 2-10% w/w of the film conveys the desired flexibility.

Surprisingly it appeared that a moisture content of 2-10% w/w for sufficiently ensuring flexibility can permanently be maintained even in very thin films if the film formulation contains a special combination of sugar alcohols.

The film according to the invention or the preparation according to the invention disintegrates within a few seconds in the oral cavity. For example, the film/the preparation is dissolved by saliva or decomposed, for example a water-soluble film is dissolved. Thus, the film or the preparation can no longer be spit out. After disintegration of the film/preparation the drug is predominantly swallowed and absorbed in the gastrointestinal tract. The drug may be partially absorbed transmucosally, this is however negligible. The film/the preparation is preferably substantially free of voids, surfactants and sherbets.

The preparation of the oral films according to the invention or the preparations according to the invention further is much cheaper than the production of for example so-called melting tablets, for which a complex lyophilization process is required, or the preparation of orally dispersible formulations, in which a bitter tasting drug is taste masked in complex processes such as microencapsulation, covering or complexation.

The film according to the invention is further characterized in that it also remains flexible over a long period of time in open storage under the conditions of climate zones II-IV and does not break when applied by the patient.

SUMMARY OF THE INVENTION

The present invention relates to:

1. a pharmaceutical film formulation comprising
   one or more bitter tasting drug(s) or pharmaceutically acceptable salts thereof,
   one or more film formers,
   one bitterness masker containing
   a) one or more inorganic and/or organic salt(s) and
   b) at least two monocyclic monoterpenes as well as
   one or more sweetener(s);

2. a pharmaceutical film formulation according to item 1, further comprising one or more humectants and/or one or more flavoring agent(s);

3. a pharmaceutical film formulation according to item 1 or 2, wherein the bitter tasting drug is selected from cetirizine, sildenafil and sumatriptane;

4. a pharmaceutical film formulation according to any of the preceding items, wherein the at least two monocyclic monoterpenes of the bitterness masker are selected from a compound of formula (A)

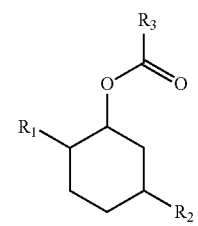

(A)

wherein $R_1$ and $R_2$ are identical or different from each other and each represent an OH group or a linear or branched $C_{1-4}$ alkyl group, preferably wherein $R_1$ is an isopropyl group and an $R_2$ is a methyl group, and $R_3$ represents a linear or branched $C_{1-4}$ alkyl or $C_{1-4}$ alkoxy group, which may optionally be substituted with an OH group, and/or
a compound of formula (B)

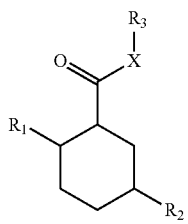

wherein
X represents O, NH or $CH_2$,
$R_1$ and $R_2$ are identical or different from each other and each represents an OH group or a linear or branched $C_{1-4}$ alkyl group, preferably wherein $R_1$ is an isopropyl group and an $R_2$ is a methyl group, and
$R_3$ represents a linear or branched $C_{1-4}$ alkyl group, which may optionally be substituted with an OH group, and/or
a compound of formula (C)

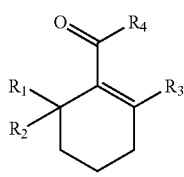

wherein
$R_1$ and $R_2$ are identical and each represent a linear or branched $C_{1-4}$ alkyl group,
$R_3$ represents a linear or branched $C_{1-4}$ alkyl group, and
$R_4$ represents a saturated or unsaturated, linear or branched $C_{1-4}$ alkyl group, preferably a 1-propenyl group or a 2-propanyl group and may optionally be substituted with an OH group;
5. a pharmaceutical film formulation according to any of the preceding items, wherein the monocyclic monoterpenes of the bitterness masker are a mixture, comprising
  (i) 1-(2,6,6-trimethylcyclohexenyl)-2-buten-1-one, preferably (Z)-1-(2,6,6-trimethyl-1-cyclohexen-1-yl)-2-buten-1-one,
  (ii) N-Ethyl-2-(isopropyl)-5-methyl cyclohexane carboxamide;
  (iii) menthyl lactate;
  (iv) menthol ethylene glycol carbonate and
  (v) menthol propylene glycol carbonate;
6. a pharmaceutical film formulation according to any of the preceding items, wherein said one or said more inorganic and/or organic salt(s) is/are selected from sodium chloride, magnesium chloride, ammonium chloride, sodium ascorbate, calcium ascorbate and sodium citrate;
7. a pharmaceutical film formulation according to any of the preceding items, wherein the bitterness masker contains
  a) one or more salt(s), selected from sodium chloride, magnesium chloride, ammonium chloride, sodium ascorbate, calcium ascorbate and sodium citrate, and
  b) a mixture comprising
    (i) (Z)-1-(2,6,6-trimethyl-1-cyclohexen-1-yl)-2-buten-1-one,
    (ii) N-ethyl-2-(isopropyl)-5-methyl cyclohexane carboxamide;
    (iii) menthyl lactate;
    (iv) menthol ethylene glycol carbonate, and
    (v) menthol propylene glycol carbonate;
8. a pharmaceutical film formulation according to any of the preceding items, wherein the bitterness masker contains sodium chloride and a mixture comprising
  (i) (Z)-1-(2,6,6-trimethyl-1-cyclohexen-1-yl)-2-buten-1-one,
  (ii) N-ethyl-2-(isopropyl)-5-methyl cyclohexane carboxamide;
  (iii) menthyl lactate;
  (iv) menthol ethylene glycol carbonate, and
  (v) menthol propylene glycol carbonate;
9. a pharmaceutical film formulation according to any of items 2-8, wherein the humectant comprises sorbitol and/or xylitol;
10. a pharmaceutical film formulation according to any one of items 2-9, wherein the humectant comprises a mixture of sorbitol and xylitol in a ratio of 1:1.5;
11. a pharmaceutical film formulation according to any of the preceding items, wherein the sweetener(s) is/are selected from sucrose, sucralose, aspartame or acesulfame potassium;
12. a pharmaceutical film formulation according to any of items 2-11, wherein the flavoring agent(s) is/are selected from grapefruit flavor, peppermint oil, peppermint flavor, levomenthol, menthol and/or low molecular weight organic acids such as citric acid, succinic acid, malic acid and adipic acid;
13. a pharmaceutical film formulation according to any of the preceding items, wherein the content of the bitter tasting drug(s) is between 0.1 and 75% w/w, related to the dry weight of the film formulation;
14. a pharmaceutical film formulation according to item 1, comprising
  one or more bitter tasting drug(s) or pharmaceutically acceptable salts thereof in an amount of at least 0.1-75% w/w,
  one or more film formers in an amount of 1-90% w/w,
  one bitterness masker, containing
    a) one or more inorganic and/or organic salt(s) in an amount of 1-10% w/w and
    b) at least two monocyclic monoterpenes in a total amount of 0.01-10% w/w and
  one or more sweetener(s) in an amount of 1-15% w/w,
  wherein the respective amounts are related to the dry weight of the film formulation;
15. a pharmaceutical film formulation according to item 14, further comprising one or more humectants in an amount of 1-10% w/w and/or one or more flavoring agent(s) in an amount of 0.01-15% w/w, wherein the respective amounts are related to the dry weight of the film formulation;
16. a pharmaceutical film formulation according to any of items 2-13 and 15, comprising
  one or more bitter tasting drug(s) selected from cetirizine, sildenafil and sumatriptan, or pharmaceutically acceptable salts thereof in an amount of up to 75% w/w,
  one or more film-formers selected from methyl cellulose, hydroxypropyl cellulose and/or hydroxypropyl methyl cellulose in an amount of 9-20% w/w
  a mixture of sorbitol and xylitol in a ratio of 1:1.5, in an amount of 2.5-5% w/w, one bitterness masker containing
  a) NaCl in an amount of 1-2% w/w
  b) (i) (Z)-1-(2,6,6-trimethyl-1-cyclohexen-1-yl)-2-buten-1-one,
    (ii) N-Ethyl-2-(isopropyl)-5-methyl cyclohexane carboxamide;
    (iii) menthyl lactate;
    (iv) menthol ethylene glycol carbonate and
    (v) menthol propylene glycol carbonate
    in a total amount of 0.01-2% w/w,
  sucralose in an amount of 2-6% w/w and
  peppermint flavor and menthol in a total amount of 0.5-7% w/w,
wherein the respective amounts are related to the dry weight of the film formulation;
17. a pharmaceutical film formulation according to any of the preceding items, characterized in that the film formulation is a non-mucoadhesive film and that the non-mucoadhesive film is a single-layer;
18. a pharmaceutical film formulation according to any of the preceding items, characterized in that it contains 50-75% w/w sildenafil citrate related to the dry weight of the film formulation as an active ingredient; and
19. the use of a combination of pharmaceutically acceptable excipients, comprising NaCl, sucralose, menthol and a mixture of
  (i) (Z)-1-(2,6,6-trimethyl-1-cyclohexen-1-yl)-2-buten-1-one,
  (ii) N-Ethyl-2-(isopropyl)-5-methyl cyclohexane carboxamide;
  (iii) menthyl lactate;
  (iv) menthol ethylene glycol carbonate and
  (v) menthol propylene glycol carbonate
for the preparation of a pharmaceutical film formulation having acceptable taste of at least one bitter tasting drug or a pharmaceutically acceptable salt thereof.

DETAILED DESCRIPTION OF THE INVENTION

The present invention relates to a pharmaceutical film formulation comprising
  one or more bitter tasting drug(s) or pharmaceutically acceptable salts thereof,
  one or more film formers,
  a bitterness masker, containing
    a) one or more inorganic and/or organic salt(s) and
    b) a plurality (at least two, preferably three, four, and in particular five) monocyclic monoterpenes as well as
  one or more sweetener(s).

In a preferred embodiment, the above pharmaceutical film formulation further contains one or more humectants, and/or one or more flavoring agent(s) capable of acting as for example taste receptor competitor(s).

Preferably, the film formulation contains one, two or three bitter tasting drugs or pharmaceutically acceptable salts thereof, more preferably one or two bitter tasting drugs or pharmaceutically acceptable salts thereof, most preferably a bitter tasting drug or a pharmaceutically acceptable salt thereof.

A bitter tasting drug for the purpose of this invention is any drug that stimulates the bitter receptors of the human tongue by for example forming an association, in particular a bond, with the bitter receptors, such that a nerve impulse is triggered, which produces an (unpleasant) bitter taste sensation.

Preferably the bitter tasting drug(s) is/are selected from cetirizine, anti-migraine agents, such as sumatriptan, almotriptan, avitriptan, eletriptan, frovatriptan, naratriptan, rizatriptan and zolmitriptan, and PDE-V inhibitors such as sildenafil, tadalafil and vardenafil, or pharmaceutically acceptable salts thereof.

More preferably, the bitter tasting drug(s) is/are cetirizine, sumatriptan, almotriptan, avitriptan, eletriptan, frovatriptan, naratriptan, rizatriptan, zolmitriptan, sildenafil, tadalafil and/or vardenafil or pharmaceutically acceptable salts thereof.

Even more preferred the bitter tasting drug(s) is/are cetirizine, sumatriptan, sumatriptan succinate, sildenafil and sildenafil citrate.

Most preferred the bitter tasting drug is sildenafil or sildenafil citrate.

The drug content in the inventive film formulations is at least 0.1 to 75% w/w, preferably at least 20 to 75% w/w, more preferably at least 60 to 75% w/w and preferably 60 or up to 60% w/w and particularly preferably 75% or up to 75 w/w, related to the dry weight of the film formulation.

The inventive film formulation contains one or more film formers, preferably one film former.

A film former within the meaning of this invention is a substance that is able to form the matrix of a film, in particular a substance, which confers the film formulation a certain degree of flexibility in the mechanical properties, such as restoring force, flexural modulus, tensile modulus, and the like.

For the inventive film formulation one or more film formers may be used, which are selected from:
  polymeric carbohydrates such as cellulose and its derivatives, starch and its derivatives, agar-agar, alginic acid, arabinogalactan, galactomannan, carrageenan, dextran, tragacanth and gums of vegetable origin,
  synthetic polymers, which are preferably water-soluble or swellable, such as polyvinylpyrrolidone, polyvinyl alcohol, polyacrylic acid or polyacrylamide, and
  polypeptides, such as gelatin, albumin or collagen, or mixtures thereof.

Preferably methyl cellulose (MC), hydroxypropyl cellulose (HPC) or hydroxypropyl methyl cellulose (HPMC), carboxymethyl cellulose, starch or modified starch, pullulan, pectin and/or gelatin may be used as film formers. In particular preferred is/are MC and/or HPC and/or HPMC used as film formers. Particularly preferably HPC is used as film former.

In the case of MC this has preferably a weight-average molecular weight of 25,000 to 400,000 g/mol.

The weight-average molecular weight is determined in the present application by means of gel permeation chromatography.

In the case of HPC this preferably has a weight-average molecular weight of 50,000 to 1,250,000 g/mol, more preferably of 70,000 to 500,000 g/mol.

Preferably a HPC with a softening temperature of 110 to 150° C. is used.

Preferably, the used HPC has a water content of 2 to 12% w/w. A particularly preferred HPC has all of these properties at the same time and has a weight-average molecular weight of 70,000 to 500,000 g/mol.

In the case of HPMC this preferably has a weight-average molecular weight of 10,000 to 1,500,000 g/mol, more preferably of 50,000 to 500,000 g/mol.

Further preferred a HPMC with a glass transition temperature (Tg) of 160 to 190° C. is used, which preferably has a water content of 1 to 15% w/w and particularly preferably has a weight-average molecular weight of 50,000 to 500,000 g/mol.

In the case of carboxymethyl cellulose this preferably has a weight-average molecular weight of 90,000 to 700,000 g/mol, more preferably of 110,000 to 450,000 g/mol.

Further preferred a carboxymethyl cellulose having a water content of 0.1 to 10% w/w is used, which particularly preferably has a weight-average molecular weight of 110,000 to 450,000 g/mol.

In the case of starch or modified starch this preferably has a weight-average molecular weight of 50,000 to 160,000 g/mol, more preferably of 55,000 to 150,000 g/mol.

Further preferred a starch or modified starch with a water content of 8 to 15% w/w is used, which particularly preferably has a weight-average molecular weight of 55,000 to 150,000 g/mol.

In the case of pullulan (1,6-alpha-maltotriose) this preferably has a weight-average molecular weight of 8,000 to 2,000,000 g/mol, more preferably of 20,000 to 900,000 g/mol.

Further preferred a pullulan with a water content of 0.1 to 6% w/w is used, which particularly preferably has a weight-average molecular weight of 20,000 to 900,000 g/mol.

In the case of pectin this preferably has a weight average-molecular weight of 30,000 to 100,000 g/mol, more preferably of 35,000 to 90,000 g/mol.

Further preferred a pectin with a melting point of 140–160° C. (in the dry state) is used, which particularly preferably has a weight-average molecular weight of 35,000 to 90,000 g/mol.

In the case of gelatine this preferably has a weight-average molecular weight of 15,000 to 250,000 g/mol, more preferably of 25,000 to 150,000 g/mol.

Further preferred a gelatin with a water content of 8 to 12% w/w is used, which particularly preferably has a weight-average molecular weight of 25,000 to 150,000 g/mol.

In the case of polyvinylpyrrolidone, this can be obtained, for example by polymerization of N-vinylpyrrolidone-2.

Preferably the polyvinylpyrrolidone has a weight-average molecular weight of 5.000 to 100,000 g/mol, more preferably of 8,000 to 80,000 g/mol, particularly preferably of 10,000 g/mol to 40,000 g/mol.

In the case of polyvinyl alcohol that is produced for example by hydrolytic cleavage of polyvinyl esters with alkalis.

Preferably, the polyvinyl alcohol has a weight-average molecular weight of 20,000 to 220,000 g/mol, more preferably of 25,000 to 100,000 g/mol, particularly preferably of 28,000 g/mol to 40,000 g/mol.

The content of film formers in the inventive film formulations is from 1 to 90% w/w, preferably 5 to 60% w/w, more preferably 8 to 40% w/w, more preferably 9 to 20% w/w, related to the dry weight of the film formulation.

In a preferred embodiment, the inventive film formulation contains one or more humectants.

The humectants ensure a certain moisture content in the final film formulations of the present invention.

A certain moisture content is necessary in order to ensure that the film does not break during the manufacture, packaging, transport and application, but instead remains flexible.

Preferably the moisture content is 0.5-10% w/w, more preferably 1-15% w/w and most preferably 2-10% w/w, related to the dry weight of the inventive film formulations.

The humectant(s) for use in the inventive film formulations is/are selected from sugar alcohols such as sorbitol and xylitol.

Preferably a combination of sorbitol and xylitol is used as humectant.

The weight ratio of sorbitol and xylitol is preferably 1:1.5.

The total amount of humectant in the inventive film formulations is 1-10% w/w, preferably 2.5-5% w/w, each related to the dry weight of the film formulations.

The inventive film formulation contains a special combination
of a bitterness masker containing
a) one or more inorganic and/or organic salt(s) and
b) a plurality (at least two, in particular three, four, and preferably five) monocyclic monoterpenes,
and
optionally one or more sweetener(s) and/or one or more flavoring agent(s) for effective taste masking of extremely bitter tasting drugs, which are incorporated into the inventive film formulations.

With taste masking under the scope of the present invention, the coverage of the unpleasant and in particular the bitter taste of a substance, such as a drug, is understood.

Suitable inorganic salts for use in the inventive film formulations are halide salts of sodium, potassium, calcium, magnesium and ammonium, preferably sodium chloride, magnesium chloride and ammonium chloride.

Suitable organic salts for use in the inventive film formulations are the salts of ascorbic acid and citric acid, preferably sodium ascorbate, calcium ascorbate, and sodium citrate.

In a particularly preferred embodiment, the inventive film formulations contain sodium chloride.

The total amount of inorganic and/or organic salt(s) in the inventive film formulations is 0.5-10% w/w, preferably 1-5% w/w, and more preferably 1-2% w/w, each related to the dry weight of the film formulations.

Suitable monocyclic monoterpenes for use in the inventive film formulations are selected from
a compound of formula (A)

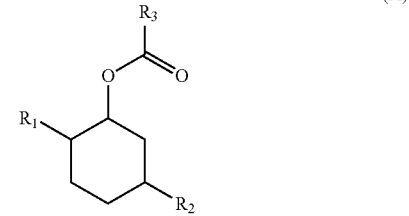

wherein
$R_1$ and $R_2$ are identical or different from each other and each represent an OH group or a linear or branched $C_{1-4}$ alkyl group, in which preferably $R_1$ is a isopropyl group and $R_2$ is a methyl group, and
$R_3$ represents a linear or branched $C_{1-4}$ alkyl or $C_{1-4}$ alkoxy group, which may optionally be substituted with an OH group; and/or
a compound of formula (B)

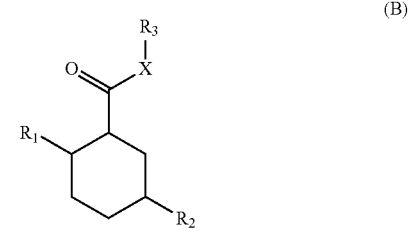

wherein
X represents O, NH or $CH_2$,
$R_1$ and $R_2$ are identical or different from each other and each represents an OH group or a linear or branched $C_{1-4}$ alkyl group, in which preferably $R_1$ is an isopropyl group and $R_2$ is a methyl group, and
$R_3$ represents a linear or branched $C_{1-4}$ alkyl group, which may optionally be substituted with an OH group; and/or
a compound of formula (C)

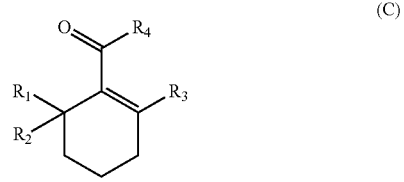

wherein
$R_1$ and $R_2$ are identical and each represents a linear or branched $C_{1-4}$ alkyl group,
$R_3$ represents an OH group or a linear or branched $C_{1-4}$ alkyl group, and
$R_4$ is a saturated or unsaturated, linear or branched $C_{1-4}$ alkyl group, preferably represents a 1-propenyl or a 2-propenyl group, and may optionally be substituted with an OH group;
in which the compounds of formulas (A), (B) and (C) comprises both the pure enantiomers and/or cis-trans isomers as well as the respective mixtures thereof.
Preferably
1-(2,6,6-trimethylcyclohexenyl)-2-buten-1-one and in this case particularly (Z)-1-(2,6,6-Trimethyl-1-cyclohexen-1-yl)-2-buten-1-one,
N-ethyl-2-(isopropyl)-5-methyl cyclohexane carboxamide;
menthyl lactate;
menthol ethylene glycol carbonate and
menthol propylene glycol carbonate;
are used as monocyclic monoterpenes in the bitterness masker of the inventive film formulations.

The bitterness masker of the inventive film formulations contains several monocyclic monoterpenes. Thereby "several" monocyclic monoterpenes means at least two, in particular three, four, and preferably five monocyclic monoterpenes.

More preferably, the bitterness masker of the inventive film formulations contains a mixture of monocyclic monoterpenes of
(Z)-1-(2,6,6-trimethyl-1-cyclohexen-1-yl)-2-buten-1-one,
N-ethyl-2-(isopropyl)-5-methylcyclohexane carboxamide,
menthyl lactate,
menthol ethylene glycol carbonate and
menthol propylene glycol carbonate.

The total amount of the monocyclic monoterpenes in the inventive film formulations is 0.01-10% w/w, preferably 0.01-5% w/w and more preferably 0.01-2% w/w, each related to the dry weight of the film formulations.

The weight ratio of the inorganic and or organic salt(s) to the monocyclic monoterpenes in the bitterness masker of the inventive film formulations is 1/10-10/1, preferably 1/3-3/1, more preferably 1/1, and most preferably 1/0.2-0.2/1.

As sweeteners for use in the inventive film formulations both substances are suitable whose sweetness effect occurs immediately, as well as substances whose sweetness effect occurs after a delay.

Suitable sweeteners are natural and synthetic sweeteners.
Suitable natural sweeteners are monosaccharides, disaccharides and polysaccharides, especially sucrose, as well as natural protein-based sweeteners such as thaumatin and monellin.

Suitable synthetic sweeteners are saccharin, cyclamate, sucralose, acesulfame potassium as well as synthetic protein-based sweeteners, such as aspartame.

Preferably, the inventive film formulations contains sucralose, aspartame or acesulfame potassium, preferably sucralose.

The total amount of the sweetener(s) in the inventive film formulations is 1-15% w/w, preferably 1-10% w/w, and more preferably 2-6% w/w, each related to the dry weight of the film formulations.

In a preferred embodiment, the inventive film formulation contains one or more flavoring agent(s).

Suitable flavoring agents for use in the inventive film formulations are natural and artificial flavoring agents suitable for consumption, especially orange, strawberry, vanilla, grapefruit flavor, peppermint oil, peppermint flavor, and cinnamyl acetate, citral, citronella, eugenyle format, methyl anisole, levomenthol and menthol as well as low molecular weight organic acids such as citric acid, succinic acid, malic acid and adipic acid.

The total amount of the flavoring agent(s) in the inventive film formulations is 0.01-15% w/w, preferably 0.05-10% w/w, and more preferably 0.5-7% w/w, each related to the dry weight of the film formulations.

The total amount of the combination of a bitterness masker, comprising a) one or more inorganic and/or organic salt(s) and b) at least two monocyclic monoterpenes, and one or more sweetener(s) and optionally one or more flavoring agent(s) in the inventive film formulations is 2-20% w/w, preferably 2-15% w/w, and more preferably 2-7% w/w, each related to the dry weight of the film formulations.

In a preferred embodiment, the inventive film formulation comprises:
one or more bitter tasting(s) drug(s) or pharmaceutically acceptable salts thereof in an amount of at least 0.1-75% w/w,
one or more film former(s) in an amount of 1-90% w/w,
a bitterness masker containing
a) one or more inorganic and/or organic salt(s) in an amount of 1-10% w/w, and
b) at least two monocyclic monoterpenes in a total amount of 0.01-10% w/w as well as
one or more sweetener(s) in an amount of 1-15% w/w,
in which the respective amounts are related to the dry weight of the film formulation.

Preferably the above inventive film formulation also contains one or more humectants in an amount of 1-10% w/w and/or one or more flavoring agent(s) in an amount of 0.01-15% w/w each related to the dry weight of the film formulation.

Particularly preferably, the inventive film formulation comprises:
one or more bitter tasting drug(s), selected from cetirizine, sildenafil and sumatriptan, or pharmaceutically acceptable salts thereof in an amount of up to 75% w/w,
one or more film former(s) selected from methyl cellulose, hydroxypropyl cellulose and/or hydroxypropyl methyl cellulose in an amount of 9-20% w/w, a mixture of sorbitol and xylitol as humectant in a ratio of 1:1.5, in an amount of 2.5-5% w/w, a bitterness masker containing a) NaCl in an amount of 1-2% w/w, and b) (Z)-1-(2,6,6-trimethyl-1-cyclohexen-1-yl)-2-buten-1-one, N-ethyl-2-(isopropyl)-5-methylcyclohexane carboxamide, menthyl lactate, menthol ethylene glycol carbonate and menthol propylene glycol carbonate in a total amount of 1-2% w/w, sucralose in an amount of 2-6% w/w, and peppermint flavor and menthol in a total amount of 0.5-7% w/w in which the respective amounts are related to the dry weight of the film formulation.

In a further embodiment, the inventive film formulation also contains one or more preservatives, dye(s) and/or filler(s).

Suitable preservatives for use in the inventive film formulations are, for example sorbic acid and salts thereof.

As dyes in the inventive film formulations conventional pharmaceutical dyes and pigments may be used, in particular FD & C Blue No. 1 Brilliant Blue ("Blaulack") and FD & C Blue No. 2 Indigo Carmine ("Blaulack") or any mixture thereof as well as $TiO_2$, $Fe_xO_x$, β-carotene, carmoisine, indigo carmine, riboflavin and the like.

Suitable fillers for use in the inventive film formulations are salts such as, carbonates and phosphates, oxides, such as, for example $SiO_2$, in particular in the form of Aerosil, or the like and/or cellulose and its derivatives, as well as poorly soluble sugars or sugar derivatives, such as lactose or starch derivatives, such as, for example cyclodextrins, if those are available in the final inventive film formulation essentially undissolved and thus fulfill the mechanical properties of a filler. Preferably microcrystalline cellulose is used as filler.

The total amount of preservatives, dyes and/or fillers in the inventive film formulations is from 0.1 to 60% w/w, preferably from 0.5 to 50% w/w and more preferably from 4 to 50% w/w, each related to the dry weight of the film formulations.

In a preferred embodiment, the inventive film formulation is a monolayer, and preferably substantially free of voids, surfactants, and sherbets.

Preferably, the inventive film formulation is a film, in particular a solid film.

The inventive film formulation is characterized by a very advantageous combination of mechanical stability of the film and rapid release of the drug. Preferably, the inventive film formulation rapidly disintegrates in saliva.

The term "monolayer film formulation" means a solid preparation which is in the form of a single film. Therein monolayer means, that the film is in the form of a single layer, wherein the layer is preferably homogeneous. The film can be flexible or non-flexible. Preferably, the film is flexible.

Preferably, the inventive mono-layer film formulation is substantially free of voids. In this case a void is understood as an area which is filled with a fluid such as gas and/or liquid. Such a cavity has a diameter of typically less than 100 micrometer.

The use of surfactants is disadvantageous due to the possible irritant effect on skin or mucosa. In addition, many of the common surfactants are tasting very bitter. Disadvantageous is also a possible interaction with the drug absorption in the gastrointestinal tract.

Preferably, the inventive monolayer film formulation is therefore substantially free of surfactants. Therein substantially free of surfactants means that the film formulations contains less than 1% w/w, preferably less than 0.1% w/w and most preferably less than 0.01% w/w of surfactant, each related to the dry weight of the film formulations. In particular in the production of the inventive film formulation no surfactants are added as ingredient. A surfactant in the context of this invention is any conventional surfactant or wetting agent or any surfactant substance.

Preferably, the inventive monolayer film formulation is also substantially free of effervescent additives. Therein substantially free of effervescent additives means that the film formulations contains less than 1% w/w, preferably less than 0.1% w/w and most preferably less than 0.01% w/w effervescent additives, each related to the dry weight of the film formulations. In particular in the production of the inventive film formulation no effervescent additive is added as an ingredient. An effervescent additive within the scope of this invention is a compound which upon addition of water, during storage, at elevated temperature or the like, releases a gaseous compound. Preferably an effervescent additive is a compound which, in the mouth, for example by the action of saliva, releases a gaseous compound, such as a carbon dioxide former. The film formulations contain thus no or almost no effervescent additive, such as a carbon dioxide former.

The film thickness of the inventive film formulation is from 5 to 500 micrometer, preferably from 5 to 400 micrometer, and more preferably from 5 to 300 micrometer.

The inventive film formulation can be available as round, any rounded, oval, elliptical, triangular, square, for example square or rectangular, or polygonal film. Preferably, the inventive film formulation is square or rectangular.

The inventive film formulation may have a smooth surface or a surface with elevations and/or depressions. Preferably, the surface of the inventive film formulation has a regular pattern of projections and depressions, such as a wave pattern or a grid pattern.

The disintegration time of the inventive film formulation in the oral cavity is 1-100 seconds, preferably 1-50 seconds, more preferably 1-10 seconds.

In one embodiment, the inventive film formulation can be present on a carrier sheet.

Preferably, the support film on which the film according to the invention formulation is present is a carrier film made from polyethylene paper (PE paper), polypropylene foil (PP foil) and polyethylene terephthalate film (PET film).

In a preferred embodiment, the inventive film formulation is intended for oral administration.

In a further preferred embodiment, the inventive film formulation for oral administration is a non-mucoadhesive film.

In one embodiment of the present invention, the inventive film formulation is packed in a sachet bag. The present invention therefore also relates to sachet bags with one or more of the inventive film formulations.

In a further embodiment of the present invention, the inventive film formulation is packaged in multidose containers. The present invention therefore also relates to multidose containers with a plurality of the inventive film formulations.

To prepare the inventive film formulation the bitter tasting drug(s) is (are) dissolved or suspended in a solvent. As a solvent, organic solvents such as alcohols, ketones, etc., or water or mixtures thereof can be used.

Suitable solvents are, for example, ethanol, acetone and ethanol/water mixtures or acetone/water mixtures.

After addition of one or more film former(s), one or more humectant(s), the bitterness masker, one or more sweetener(s), optionally one or more flavoring agent(s) and optionally one or more gustatory substance(s), dye(s), preservative(s) and/or filler(s) the mixture is homogenized. The mixture is coated with a suitable coating method onto a support material. As support material, for example, PE paper, PP or PET film can be used. The coated substrate is dried at 30 to 120° C., preferably at 30 to 70° C. Then the coated carrier material is further processed into divided films with defined area. This can be done by punching, cutting or stamping. The films are packed individually with or without support foil in sachet bags or multidose containers. Before the intake of the inventive drug-containing film formulation it is possibly peeled off from the support material.

In one embodiment, the inventive film formulation is used for the administration of cetirizine for allergic symptoms, for the administration of anti-migraine drugs in the (acute) treatment of migraine attacks with or without aura and the like, or for administration of PDE-V inhibitors in the treatment of erectile dysfunction.

In a further embodiment, the inventive film formulation is used for preparing a medicament for the alleviation of allergic symptoms, for the treatment of migraine with and without aura and the like, and for the treatment of erectile dysfunction.

The present invention also relates to the use of the above described particular combination of a bitterness masker containing one or more inorganic and/or organic salt(s) as well as several monocyclic monoterpenes, and one or more sweetener(s) and optionally one or more flavoring agent(s) to mask the taste of bitter tasting substances, and in particular to mask the taste of one or more bitter tasting drug(s) or pharmaceutically acceptable salts thereof.

In a preferred embodiment, the present invention provides the use of the above described particular combination of a bitterness masker containing one or more inorganic and/or organic salt(s) as well as several monocyclic monoterpenes, and one or more sweetener(s) and optionally one or more flavoring agent(s) to prepare a pharmaceutical film formulation having an acceptable taste of bitter tasting substances, in particular of one or more bitter tasting drug(s) or pharmaceutically acceptable salts thereof.

In particular the present invention relates to the use of a combination of pharmaceutically acceptable excipients, comprising NaCl, sucralose, menthol, and a mixture of monocyclic monoterpenes from (Z)-1-(2,6,6-trimethyl-1-cyclohexen-1-yl)-2-buten-1-one, N-ethyl-2-(isopropyl)-5-methyl cyclohexane carboxamide, menthyl lactate, menthol ethylene glycol carbonate and menthol propylene glycol carbonate for the preparation of a pharmaceutical film formulation having acceptable taste of at least one bitter tasting drug, or a pharmaceutically acceptable salt thereof.

The disclosure of the present application also includes in particular any combinations of each of the described embodiments of the individual features of the inventive film formulation and of all preferred embodiments with each other, i.e. the present application discloses, for example also an inventive film formulation comprising a bitter tasting drug in an amount of 60% w/w or 75% w/w,
one or more film formers in an amount of 1-90% w/w,
a mixture of sorbitol and xylitol as a humectant in a ratio of 1:1.5, in an amount of 2.5-5% w/w,
a bitterness masker, containing
 a) one or more inorganic and/or organic salt(s) in an amount of 1-5% w/w, and
 b) at least two monocyclic monoterpenes in a total amount of 0.01-2% w/w, and
a sweetener in an amount of 2-6% w/w,
peppermint flavor and menthol in a total amount of 0.01-15% w/w, and
one or more flavoring agent(s), preservatives, dye(s) and/or filler(s) in a total amount of 4 to 50% w/w,
in which the respective amounts being related to the dry weight of the film formulation.

Also the present application discloses any combinations of individual features of the below described examples of the inventive film formulation with specific embodiments of the individual features of the inventive film formulation according to the above description.

As far as in the present application number ranges are disclosed, the disclosure of the present application comprises not only the respective number ranges and their final values as such, but all numerical values lying within the disclosed number ranges, i. e., all intermediate values of such number ranges and all combinations of the intermediate values of various number ranges.

By the term "comprised/comprising" in the context of the inventive pharmaceutical film formulation both formulations are meant that in addition to the ingredients listed contain further ingredients as well as formulations containing only the components listed.

The same applies for the term "contains/containing" which is generally to be understood open, but should also include in a preferred variant the possibility that the respective inventive pharmaceutical film formulations only contain the specified components and no additional components.

The invention is explained in more detail by the following examples without limiting the scope of the invention.

Unless otherwise indicated, all references in % w/w are related to the dry weight of the respective film formulations.

EXAMPLES

Preparation

Example 1

Composition:

| Ingredient | Amount [%] |
|---|---|
| Active substance | |
| Sildenafil citrate | 66.90 |
| Excipients | |
| Aerosil | 1.00 |
| Peppermint | 6.00 |
| Menthol | 1.00 |
| Sucralose | 6.00 |
| Contramarum forte * | 1.50 |
| HPC (Klucel EF) | 9.50 |
| NaCl | 1.90 |
| Glycerol | 3.20 |
| Sorbitol | 1.00 |
| Xylitol | 1.50 |
| "Blaulack" | 0.50 |
| | 100.00 |

| Solvent | Add per 1 cm$^3$ Preparation [mg] |
|---|---|
| Ethanol 96% | 12.50 |
| Purified water | 12.50 |

* contains a mixture of (Z)-1-(2,6,6-trimethyl-1-cyclohexen-1-yl)-2-buten-1-one, N-ethyl-2-(isopropyl)-5-methyl cyclohexane carboxamide, menthyl lactate, and menthol ethylene glycol carbonate and menthol propylene glycol carbonate Preparation of the Coating Composition:
Solution 1: Aerosil, peppermint, menthol, sucralose, contramarum forte, glycerol and ethanol are weighed and stirred for 10 minutes. HPC is weighed and added with stirring to the resulting solution. Subsequently, the sildenafil citrate is weighed and so added to the resulting solution.

Solution 2: sodium chloride, sorbitol, xylitol, "blaulack" and water are weighed into a second vessel, and dissolved with stirring.

Solution 2 is then added to solution 1 and stirred until further processing continues (at least approximately 6 hours).

Example 2

Composition:

| Ingredient | Amount [%] |
|---|---|
| Active substance | |
| Sildenafil citrate | 66.90 |
| Excipients | |
| Aerosil | 1.00 |
| Peppermint | 6.00 |
| Menthol | 1.00 |
| Sucralose | 6.00 |
| Contramarum forte * | 1.50 |
| HPMC (Metolose 60SH 50) | 9.95 |
| NaCl | 1.90 |
| Glycerol 87% | 3.00 |
| Sorbitol | 1.00 |
| Xylitol | 1.50 |
| "Blaulack" | 0.25 |
| | 100.00 |

| Solvent | Add per 1 cm³ Preparation [mg] |
|---|---|
| Ethanol 96% | 15.00 |
| Purified water | 12.50 |

* contains a mixture of (Z)-1-(2,6,6-trimethyl-1-cyclohexen-1-yl)-2-buten-1-one, N-ethyl-2-(isopropyl)-5-methyl cyclohexane carboxamide, menthyl lactate, and menthol ethylene glycol carbonate and menthol propylene glycol carbonate Preparation of the Coating Composition:

Solution 1: Aerosil, peppermint, menthol, sucralose, contramarum forte, glycerol 87% and ethanol are weighed and stirred for 10 minutes. HPMC is weighed and added with stirring to the resulting solution. Subsequently, the sildenafil citrate is weighed and added to the resulting solution.

Solution 2: sodium chloride, sorbitol, xylitol, "Blaulack" and water are weighed into a second vessel, and dissolved with stirring.

The solution 2 is then added to solution 1 and stirred until further processing continues (at least approximately 6 hours).

Example 3

Composition:

| Ingredient | Amount [%] |
|---|---|
| Active substance | |
| Sildenafil citrate | 66.90 |
| Excipients | |
| Aerosil | 1.00 |
| Peppermint | 6.00 |
| Menthol | 1.00 |
| Sucralose | 6.00 |
| Contramarum forte * | 1.50 |
| HPMC (Metolose 60SH 50) | 10.20 |
| NaCl | 1.90 |
| Glycerol 87% | 3.00 |
| Sorbitol | 2.50 |
| | 100.00 |

| Solvent | Add per 1 cm³ Preparation [mg] |
|---|---|
| Ethanol 96% | 15.00 |
| Purified water | 12.50 |

* contains a mixture of (Z)-1-(2,6,6-trimethyl-1-cyclohexen-1-yl)-2-buten-1-one, N-ethyl-2-(isopropyl)-5-methyl cyclohexane carboxamide, menthyl lactate, and menthol ethylene glycol carbonate and menthol propylene glycol carbonate Preparation of the Coating Composition:

Solution 1: menthol, peppermint flavor, and ethanol are weighed and stirred until menthol is dissolved (about 3 minutes). Metolose 60SH 50 is weighed and added with stirring to the resulting solution.

Solution 2: sucralose, sorbitol, NaCl, contramarum forte, Aerosil, glycerin and water are weighed and dissolved with stirring (15 min). The resulting solution remains cloudy milky.

Solution 2 is added with stirring to solution 1.

Subsequently, the sildenafil citrate is weighed and added to the resulting solution and the mixture is stirred overnight (at least approximately 6 hours).

Example 4

Composition:

| Ingredient | Amount [%] |
|---|---|
| Active substance | |
| Sildenafil citrate | 66.90 |
| Excipients | |
| MCC | 2.50 |
| Peppermint | 6.00 |
| Menthol | 1.50 |
| Sucralose | 5.50 |
| Contramarum forte * | 2.00 |
| HPC (Klucel EF) | 12.05 |
| NaCl | 1.50 |
| Dibutyl sebacate | 2.00 |
| Blue dye | 0.05 |
| | 100.00 |

| Solvent | Add per 1 cm³ Preparation [mg] |
|---|---|
| Acetone | 12.00 |
| Purified water | 4.00 |

* contains a mixture of (Z)-1-(2,6,6-trimethyl-1-cyclohexen-1-yl)-2-buten-1-one, N-ethyl-2-(isopropyl)-5-methyl cyclohexane carboxamide, menthyl lactate, and menthol ethylene glycol carbonate and menthol propylene glycol carbonate Preparation of the Coating Composition:

Solution 1: MCC, peppermint, menthol, sucralose, contramarum forte, dibutyl sebacate and acetone are weighed and stirred for 10 minutes. HPC is weighed and added with stirring to the resulting solution. Subsequently, the sildenafil citrate is weighed and added to the resulting solution.

Solution 2: sodium chloride, blue dye and water are weighed into a second vessel, and dissolved with stirring.

The solution 2 is then added to solution 1 and stirred until further processing continues (at least approximately 6 hours).

Taste Masking

All films prepared according to Examples 1-4 are characterized by excellent handling, rapid disintegration in the mouth and a pleasant taste and a very good masking of the bitter taste of each of the contained drugs.

The invention claimed is:

1. A pharmaceutical film formulation comprising:
   from 60% w/w to 75% w/w of sildenafil or pharmaceutically acceptable salts thereof;
   from 9% w/w to 20% w/w of hydroxypropylcellulose;
   a bitterness masker comprising:
      a) from 1% w/w to 5% w/w of one or more inorganic salt(s); and
      b) from 0.01% w/w to 2% w/w of monocyclic monoterpenes comprising N-ethyl-2 (isopropyl)-5-methyl cyclohexane carboxamide and menthol ethylene glycol carbonate;
   from 2% w/w to 6% w/w of one or more sweeteners; and
   from 0.01% w/w to 15% w/w of one or more flavoring agents,
      wherein the respective amounts are based on the dry weight of the film formulation, and
      wherein the film is substantially free of voids.

2. The pharmaceutical film formulation according to claim 1, wherein said one or said more inorganic salt(s) is/are selected from the group consisting of sodium citrate, sodium chloride, magnesium chloride, and ammonium chloride.

3. The pharmaceutical film formulation according to claim 1, wherein the monocyclic monoterpenes of the bitterness masker are a mixture comprising:
   (i) 1-(2,6,6-trimethylcyclohexenyl)-2-buten-1-one;
   (ii) N-Ethyl-2-(isopropyl)-5-methyl cyclohexane carboxamide;
   (iii) menthyl lactate;
   (iv) menthol ethylene glycol carbonate; and
   (v) menthol propylene glycol carbonate.

4. The pharmaceutical film formulation according to claim 2, wherein said inorganic salt is sodium chloride.

5. The pharmaceutical film formulation according to claim 1, wherein the bitterness masker contains
   a) one or more salt(s) selected from the group consisting of sodium chloride, magnesium chloride, ammonium chloride, sodium ascorbate, calcium ascorbate, and sodium citrate, and
   b) a mixture comprising:
      (i) (Z)-1-(2,6,6-trimethyl-1-cyclohexen-1-yl)-2-buten-1-one;
      (ii) N-ethyl-2-(isopropyl)-5-methyl cyclohexane carboxamide;
      (iii) menthyl lactate;
      (iv) menthol ethylene glycol carbonate; and
      (v) menthol propylene glycol carbonate.

6. The pharmaceutical film formulation according to claim 1, wherein the bitterness masker contains sodium chloride and a mixture comprising:
   (i) (Z)-1-(2,6,6-trimethyl-1-cyclohexen-1-yl)-2-buten-1-one;
   (ii) N-ethyl-2-(isopropyl)-5-methyl cyclohexane carboxamide;
   (iii) menthyl lactate;
   (iv) menthol ethylene glycol carbonate; and
   (v) menthol propylene glycol carbonate.

7. The pharmaceutical film formulation according to claim 1, wherein the sweetener(s) is/are selected from the group consisting of sucrose, sucralose, aspartame, and acesulfame potassium.

8. The pharmaceutical film formulation according to claim 1, wherein the one or more flavoring agent(s) is/are selected from the group consisting of grapefruit flavor, peppermint oil, peppermint flavor, levomenthol, menthol, and organic acids.

9. The pharmaceutical film formulation according to claim 1, wherein the film formulation is a non-mucoadhesive film and wherein the non-mucoadhesive film is a monolayer.

10. A pharmaceutical film formulation comprising:
    from 60% w/w to 75% w/w of sildenafil or pharmaceutically acceptable salts thereof,
    from 9% w/w to 20% w/w of hydroxypropylcellulose,
    a bitterness masker comprising:
       a) from 1% w/w to 5% w/w of one or more inorganic salt(s); and
       b) from 0.01% w/w to 2% w/w of monocyclic monoterpenes comprising N-ethyl-2 (isopropyl)-5-methyl cyclohexane carboxamide and menthol ethylene glycol carbonate;
    from 2% w/w to 6% w/w of one or more sweeteners;
    from 0.01% w/w to 15% w/w of one or more flavoring agents; and
    from 2.5 to 5% w/w of humectants comprising sorbitol and xylitol, wherein the humectants maintain the moisture content of the film formulation in a range of between 5 and 10% w/w,
       wherein the respective amounts of are based on the dry weight of the film formulation, and
       wherein the film is substantially free of voids.

11. The pharmaceutical film formulation according to claim 10, wherein said one or said more inorganic salt(s) is/are selected from the group consisting of sodium citrate, sodium chloride, magnesium chloride, and ammonium chloride.

12. The pharmaceutical film formulation according to claim 10, wherein the monocyclic monoterpenes of the bitterness masker are a mixture comprising:
    (i) 1-(2,6,6-trimethylcyclohexenyl)-2-buten-1-one;
    (ii) N-Ethyl-2-(isopropyl)-5-methyl cyclohexane carboxamide;
    (iii) menthyl lactate;
    (iv) menthol ethylene glycol carbonate; and
    (v) menthol propylene glycol carbonate.

13. The pharmaceutical film formulation according to claim 11, wherein said inorganic salt is sodium chloride.

14. The pharmaceutical film formulation according to claim 10, wherein the bitterness masker comprises:
    a) one or more salt(s) selected from the group consisting of sodium chloride, magnesium chloride, ammonium chloride, sodium ascorbate, calcium ascorbate and sodium citrate, and
    b) a mixture comprising:
       (i) (Z)-1-(2,6,6-trimethyl-1-cyclohexen-1-yl)-2-buten-1-one;
       (ii) N-ethyl-2-(isopropyl)-5-methyl cyclohexane carboxamide;
       (iii) menthyl lactate;
       (iv) menthol ethylene glycol carbonate; and
       (v) menthol propylene glycol carbonate.

15. The pharmaceutical film formulation according to claim 10, wherein the bitterness masker contains sodium chloride and a mixture comprising:
    (i) (Z)-1-(2,6,6-trimethyl-1-cyclohexen-1-yl)-2-buten-1-one;
    (ii) N-ethyl-2-(isopropyl)-5-methyl cyclohexane carboxamide;
    (iii) menthyl lactate;

(iv) menthol ethylene glycol carbonate; and (v) menthol propylene glycol carbonate.

16. The pharmaceutical film formulation according to claim 10, wherein the humectant comprises a mixture of sorbitol and xylitol in a ratio of 1:1.5.

17. The pharmaceutical film formulation according to claim 10, wherein the sweetener(s) is/are selected from the group consisting of sucrose, sucralose, aspartame, and acesulfame potassium.

18. The pharmaceutical film formulation according to claim 10, further comprising one or more flavoring agent(s) that is/are selected from the group consisting of grapefruit flavor, peppermint oil, peppermint flavor, levomenthol, menthol, and organic acids.

19. The pharmaceutical film formulation according to claim 1, wherein the film formulation is substantially free of surfactants.

20. The pharmaceutical film formulation according to claim 10, wherein the film formulation is substantially free of surfactants.

21. The pharmaceutical film formulation according to claim 9, wherein the non-mucoadhesive film is a solid monolayer.

22. The pharmaceutical film formulation according to claim 10, wherein the film formulation is a non-mucoadhesive film and wherein the non-mucoadhesive film is a solid monolayer.

* * * * *